United States Patent
Walele et al.

(10) Patent No.: US 7,166,739 B2
(45) Date of Patent: Jan. 23, 2007

(54) ESTERS OF MONOMETHYL BRANCHED ALCOHOLS AND PROCESS FOR PREPARING AND USING SAME IN COSMETICS AND PERSONAL CARE PRODUCTS

(75) Inventors: Ismail I. Walele, Saddle Brook, NJ (US); Samad A. Syed, Paramus, NJ (US)

(73) Assignee: Finetex, Inc., Elmwood Park, NJ (US)

( * ) Notice: Subject to any disclaimer, the term of this patent is extended or adjusted under 35 U.S.C. 154(b) by 0 days.

(21) Appl. No.: 10/757,008

(22) Filed: Jan. 14, 2004

(65) Prior Publication Data

US 2005/0014961 A1    Jan. 20, 2005

(51) Int. Cl.
  *C07C 69/78* (2006.01)
  *C07C 69/76* (2006.01)
  *C07C 69/24* (2006.01)
  *C07C 69/22* (2006.01)

(52) U.S. Cl. ............. 560/103; 560/129; 560/205; 424/64; 424/63; 514/547; 514/785; 514/873

(58) Field of Classification Search ........ 560/103, 560/129, 205; 424/64, 63; 514/547, 785, 514/873
See application file for complete search history.

(56) References Cited

U.S. PATENT DOCUMENTS

| | | | |
|---|---|---|---|
| 4,275,222 A | 6/1981 | Scala, Jr. | |
| 4,278,655 A | 7/1981 | Elmi | |
| 4,293,544 A | 10/1981 | Elmi | |
| 4,322,545 A | 3/1982 | Scala, Jr. | |
| 4,323,693 A | 4/1982 | Scala, Jr. | |
| 4,323,694 A | 4/1982 | Scala, Jr. | |
| 4,791,097 A | 12/1988 | Walele et al. | |
| 5,270,461 A | 12/1993 | Walele et al. | |
| 5,271,930 A | 12/1993 | Walele et al. | |
| 5,783,173 A | 7/1998 | Bonda et al. | |
| 5,788,954 A | 8/1998 | Bonda et al. | |
| 5,840,285 A | * 11/1998 | Fogel | |
| 2004/0076654 A1 | 4/2004 | Vinson et al. | |

FOREIGN PATENT DOCUMENTS

WO  WO 01/58411  *  8/2001
WO  WO 03/072077  *  4/2003

OTHER PUBLICATIONS

Chem Abst 113: 25693 Oct. 1989.*
Technical Data Sheet for Finsolv® Bod, Inci Name: Octyl Dodecyl Benzoate, by Finetex, Inc. dated Apr. 2000.

* cited by examiner

*Primary Examiner*—Elvis O. Price

(57) ABSTRACT

Novel benzoate, octanoate, and maleate esters of branched monomethyl C16–C17 alcohols, their process of manufacture and their use as a cosmetic ingredient for toiletry and cosmetic formulations is disclosed. The esters are useful for cosmetics and personal care cleansing products, such as skin and hair care products, and soaps.

18 Claims, No Drawings

ESTERS OF MONOMETHYL BRANCHED ALCOHOLS AND PROCESS FOR PREPARING AND USING SAME IN COSMETICS AND PERSONAL CARE PRODUCTS

BACKGROUND OF THE INVENTION

1. Field of the Invention

This invention relates generally to improved ester compositions, and more particularly to novel benzoate, octanoate, and maleate esters of monomethyl branched C16–C17 alcohols, their process of manufacture and their use as a cosmetic ingredient for toiletry and cosmetic formulations. The esters are useful for cosmetics and personal care cleansing products, such as skin and hair care products, and soaps.

2. Description of the Related Art

Esters and acids are known for a variety of different applications for cosmetic, pharmaceutical and medicinal purposes. Benzoate esters of certain alcohols and alcohol mixtures, and their uses are disclosed in assignee's U.S. Pat. Nos. 4,275,222, 4,322,545, 4,323,693, and 4,323,694 all to Scala, Jr.; U.S. Pat. Nos. 4,278,655, and 4,293,544 both to Elmi; and U.S. Pat. Nos. 5,271,930, 5,270,421, and 4,791,097 all to Walele et al. The disclosures of these patents are incorporated herein by reference.

However, none of these references teach or suggest the specific novel benzoate, octanoate and maleate esters of monomethyl branched C16–C17 alcohols of this invention or the use of such ester compositions as emollients, moisturizers, sunscreen vehicles/solvents, etc.

OBJECTS AND SUMMARY OF THE INVENTION

It is an object of this invention to provide novel benzoate, octanoate and maleate esters of monomethyl branched C16–C17 alcohols having unique properties which make them uniquely suitable for use in cosmetics, skin care products, personal care products such as creams and lotions, and in other topical applications and products.

Another object of the invention is to provide branched monomethyl C16–C17 alcohol-based benzoate, octanoate and maleate esters having superior properties, namely improved tactile properties, better spreadability, better sunscreen solubility, less tackiness (stickiness) and greasiness on the skin, better suspension properties (in TiO2), and more effectiveness in wetting and dispersing pigments.

These and other objects are obtained by reacting benzoic acid, 2-ethyl-hexanoic acid and/or maleic acid with linear/branched monomethyl C16–C17 alcohols. The compositions provided include many unique effects as compared to commercially available benzoate, octanoate and maleate ester products.

DETAILED DESCRIPTION OF THE INVENTION

The novel benzoate, octanoate and maleate esters of this invention have unique properties in that they are substantially non-greasy, lack oiliness and greasiness, have low pour points and low freezing points, have good spreadability, and are stable. These properties make the compositions useful as a vehicle or carrier, emollient or solubilizer for toiletry and cosmetic formulations such as hand creams, bath oils, antiperspirants, perfumes, colognes, cold creams, electric pre-shaves, topical pharmaceutical ointments, lipsticks, skin lotions and creams, skin moisturizers, and finger nail polish, as well as other formulations.

A particularly useful composition of this invention, particularly for use in antiperspirant compositions, sun screening compositions, creams and lotions for skin care, and the like, consists of a benzoate, octanoate and maleate ester of branched monomethyl C16 and C17 alcohols.

The branched monomethyl C16 and C17 alcohol useful in making the benzoate, octanoate and maleate esters of this invention may be represented by the following formula:

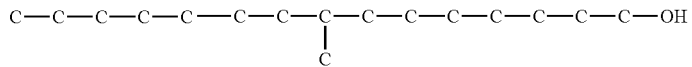

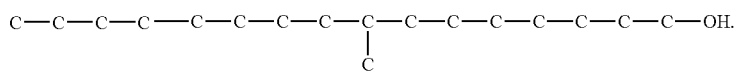

In the above formula, branching in the monomethyl branched C16 and C17 alcohol may vary from the second carbon to the fourteenth or fifteenth carbon in the linear chain.

The branched monomethyl C16 and C17 alcohol useful in making the benzoate, octanoate and maleate esters of this invention are sold under the trade name Neodol® 67 by Shell Chemical Co. (Houston, Tex.). The preferred chain distribution for the Neodol® 67 alcohol is as follows:

|     | Preferred Range | Narrow Preferred Range | Typical Preferred Range |
| --- | --- | --- | --- |
| C15 | 2%–5% | 2% | 2% |
| C16 | 28%–48% | 33%–43% | 38% |
| C17 | 33%–73% | 43%–63% | 53% |
| C18 | 4%–12% | 6%–10% | 6% |
| C19 | 1%–5% | 0%–4% | 1% |

An alpha olefin in the presence of a catalyst is converted to a mono-methyl branched internal olefin, which then undergoes a modified OXO process to form a mono-methyl branched alcohol (Neodol® 67).

The benzoate ester of branched monomethyl C16 and C17 alcohol of the invention is a C16–C17 alkyl benzoate which has the following structure:

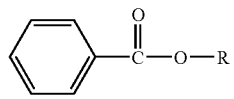

where R=monomethyl branched C16–C17 alkyl

The octanoate ester of branched monomethyl C16 and C17 alcohol of the invention is a C16–17 alkyl octanoate or C16–17 alkyl Ethylhexanoate which has the following structure:

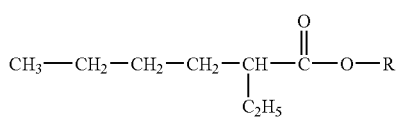

where R=monomethyl branched C16–C17 alkyl.

The maleate ester of branched monomethyl C16 and C17 alcohol of the invention is a [Di(C16–17 alkyl) maleate] which has the following structure:

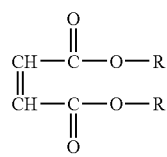

where R=monomethyl branched C16–C17 alkyl.

In manufacturing the compounds of this invention, benzoic acid or 2-ethyl hexanoic acid or maleic acid is reacted with the hydroxyl group of branched monomethyl C16 and C17 alcohol. Generally, the benzoic acid, 2-ethyl hexanoic acid or maleic acid is reacted with the branched monomethyl C16 and C17 alcohol in stoichiometric amounts with a slight excess of the benzoic acid, 2-ethyl hexanoic acid or maleic acid present. The starting materials are usually employed in stoichiometric proportions, but maybe employed in amounts corresponding to from 1 to 1, and most preferably from 1 to 0.8, but can go as low as 1 to 0.5 with excellent results. The reaction may be carried out batchwise or in a continuous manner. A batch process is preferred. A catalyst is present during the reaction. Among the catalysts which may be used are stannous oxalate, methane sulfonic acid, and the like.

The reaction is preferably conducted under an inert atmosphere of nitrogen at a reaction temperature of from 150° C. to 300° C., and preferably from 2100 to about 250° C. The acid value of the reaction is determined by procedures well known in the art. A reduced acid value indicates completion of esterification. When the acid value indicates that substantially all of the benzoic acid has been consumed, the reaction mass is then cooled to between about 70° to 80° C., and washed with water containing sodium chloride, sodium carbonate and hydrogen peroxide. The reaction mass is then vacuum dried at 125° C. with 25" Hg and then cooled to 25° C. The reaction mass is then filtered using filter aids such as diatomaceous earth or a silicate type filter aid. The products of the reaction are clear colorless liquids.

An analysis of the esters of the invention, i.e., Benzoate ester (Ref. No. 130-63); Octanoate Ester (Ref. No. 130-67); and Maleate Ester (Ref. No. 134-26), was conducted as to appearance, color, percentage water, acidity, saponification value, surface tension, spreading coefficient, freezing point, refractive index and specific gravity. The results are presented in Table I which identifies typical properties of the esters of the invention.

TABLE I

TYPICAL PROPERTIES OF ESTERS OF THE INVENTION

| Properties | Benzoate Ester (130-63) | Octanoate Ester (130-67) | Maleate Ester (134-26) |
| --- | --- | --- | --- |
| Actives % | 100% | 100% | 100% |
| Form | Liquid | Liquid | Liquid |
| Odor | Odorless | Odorless | Odorless |
| Freezing Point (° C.) | <−65 | <−65 | <−18 |
| Refractive Index @ 25° C. | 1.4840 | 1.4470 | 1.4615 |
| Surface Tension (dynes/cm) | 32 | 32.5 | 30.5 |
| Spreading Coefficient (° C.) | 33.5 | 32.5 | 34.0 |
| Viscosity, cps @ 25° C. | 60 | 44 | 80 |
| Color (APHA) | 10 | 10 | 10 |
| Water, % | 0.01 | 0.01 | 0.05 |
| Acidity (mg KOH/g) | 0.01 | 0.01 | 0.01 |
| Saponification (mg KOH/g) | 153.92 | 146.1 | 185.66 |
| Specific Gravity (25° C.) | 0.9212 | 0.8814 | 0.8950 |

The esters of the invention are useful in all types of skin care products. Hand and face creams benefit from their unique feel on the skin and spreading properties. Color cosmetics will spread easier and have better wetting and leveling effects in the dispersion of pigments. They also find use in skin care lotions and in perfumes/colognes.

The aforedescribed benzoate esters have the following properties:
1. Ease of emulsification
2. Emolliency at body temperature with good after-feel.
3. Better solubilizers for sunscreen actives
4. Lack of greasiness, pleasant skin feel
5. Lack of oiliness while imparting good lubrication
6. Low surface tension
7. Acid and alkaline stability The esters of this invention are advantageous in that they are non-oily and are useful in skin care compositions, i.e., compositions applied to the skin which soften or soothe the skin and which cosmetically affect the skin. The skin care compositions in which the esters of the invention may be used include, but are not limited to, skin creams, lotions, sun blocks, antiperspirants, deodorants, perfumes, cold creams and skin moisturizers. The foregoing list is only exemplary of the type of compositions in which the benzoate esters of this invention may be used and, as such, is not to be considered limiting.

The amount of ester used in an skin care compositions depends on the type of skin care composition desired, the type and quantity of cosmetic ingredients used and the amount and type of functional additives that are utilized. Typically, the amount of ester used ranges from about 1% to about 20% by weight of the skin care composition. The typical skin care composition further comprises one or more other components selected from the group consisting of surfactants, neutralizers, stabilizers, coloring agents, fragrances, plasticizers, foam stabilizers, film forming polymers, preservatives, antistats, sequestrants, water, dyes, perfume, thickeners, preservatives, plant extracts, and customary additive and auxiliary substances.

Preparation of the esters of the invention is illustrated by the following non-limiting examples. In the examples, as well as throughout this application, the chemical and scientific symbols have their customary meanings and all percentages are weight percentages unless otherwise specified. For ease of identification, each ester is identified by both an Example No. and a Reference No., where applicable.

EXAMPLE #1

Preparation of Benzoate Ester of Neodol® 67(Ref. No. 130-63)

In a 1000 ml. four neck round bottom flask equipped with glass stirrer, distillation head, condenser and receiver, added 400.2 grams (1.0 mole) of Neodol 67 (C16 & C17 Alcohol) and 199.8 grams (1.025 moles) of Benzoic Acid. The temperature was raised to 60° C. with a good flow of nitrogen. At 60° C., added 0.9 grams of Stannous Oxalate and continued to heat to 240° C. maintaining a good flow of nitrogen over 120 minutes, and held for 2 hours at 240° C. The distillate collected was 28 grams against theoretical estimates of 29.5 grams. The ester had the acidity of 3.8 mg. KOH/g. and it was cooled to 40° C. The crude, unwashed ester was filtered through a Filter Press with Whatman Paper #4 at 40° C. The filtered crude ester was treated with 130 grams of deionized water containing 1.30 grams of Potassium Carbonate and 2.00 grams of Potassium Chloride at 80° C. When acidity of the ester was <0.1 mg KOH/gram it was treated with 3.0 grams of hydrogen peroxide. The top layer containing the benzoate ester was collected. It was vacuum stripped at 115° C.–120° C. and 20–25 mm of Hg vacuum. The liquid benzoate of this reaction was then treated with 0.2 grams each of Magnesol (Synthetic Magnesium Silicate), Celatom FW 60 (diatomaceous earths) at 50° C. The product was filtered through a Filter Press with Whatman Paper #4. The net yield of the Benzoate Ester product was 535 grams.

EXAMPLE #2

Preparation of Octanoate Ester of Neodol 67(Ref. No. 137-67)

In a 1000 ml. four neck round bottom flask equipped with glass stirrer, distillation head, condenser and receiver, added 377.52 grams (1.0 mole) of Neodol 67 (C16 & C17 Alcohol) and 222.48 grams (1.025 moles) of 2-Ethyl Hexanoic Acid. The temperature was raised to 60° C. with a good flow of nitrogen. At 60° C., added 1.2 grams of Stannous Oxalate and continued to heat to 240° C. maintaining a good flow of nitrogen over 120 minutes, and held for 2 hours at 240° C. The distillate collected was 26.50 grams against theoretical estimates of 27.81 grams. The ester had the acidity of 6.2 mg. KOH/g. and it was cooled to 40° C. The crude, unwashed ester was filtered through a Filter Press with Whatman Paper #4 at 40° C. The filtered crude ester was treated with 112 grams of deionized water containing 3.2 grams of sodium carbonate and 11.2 grams of sodium sulfate at 80° C. When acidity of the ester was <0.1 mg KOH/gram it was treated with 3.0 grams of hydrogen peroxide. The top layer containing the octanoate ester was collected. It was vacuum stripped at 115° C.–120° C. and 20–25 mm of Hg vacuum. The liquid octanoate of this reaction was then treated with 0.2 grams each of Magnesol (Synthetic Magnesium Silicate), Celatom FW 60 (diatomaceous earths) at 50° C. The product was filtered through a Filter Press with Whatman Paper #4. The net yield of the Octanoate Ester product was 545 grams.

EXAMPLE #3

Preparation of Maleate Ester of Neodol 67(Ref. No. 134-26)

In a 1000 ml. four neck round bottom flask equipped with glass stirrer, distillation head, condenser and receiver, added 499.8 grams (2.0 moles) of Neodol 67 (C16 & C17 Alcohol) and 100.2 grams (1.025 moles) of maleic anhydride. The temperature was raised to 60° C. with a good flow of nitrogen. At 60° C., added 3.0 grams of methane sulfonic acid and continued to heat to 150° C. maintaining a good flow of nitrogen over 120 minutes, and held for 2 hours at 150° C. The distillate collected was 16 grams against theoretical estimates of 18.4 grams. The ester had the acidity of 5 mg. KOH/g. The reaction product was treated with 150 grams of deionized water containing 3.0 grams of sodium carbonate, 3 grams of hydrogen peroxide and 15 grams of sodium sulfate at 80° C. The top layer containing the maleate ester was collected. It was vacuum stripped at 115° C.–120° C. and 20–25 mm of Hg vacuum. The liquid maleate of this reaction was then treated with 0.2 grams each of Magnesol (Synthetic Magnesium Silicate), Celatom FW 60 (diatomaceous earths) at 50° C. The product was filtered through a Filter Press with Whatman Paper #4. The net yield of the Maleate Ester product was 546 grams.

Table II below compares the solubility characteristics of the esters of the invention in various solvents. The esters are soluble in most commonly used solvents, emollients and vehicles employed in cosmetic product formulations. The esters of the invention are advantageously versatile due to their Solubility/Compatibility with commonly used emollient esters, mineral oils, etc.

Table II compares the solubility characteristics of three esters of the invention, namely, benzoate ester (Ref. No. 130–63); octanoate ester (Ref. No. 130-67) and maleate ester (Ref. No. 134-26). The solubility is based on 1 gram of ester in 10 gm. solvent.

TABLE II

| Properties | Benzoate Ester (130-63) | Octanoate Ester (130-67) | Maleate Ester (134-26) |
| --- | --- | --- | --- |
| Water | − | − | − |
| Ethanol | + | + | + |
| Mineral Oil | + | + | + |
| Glycerine | − | − | − |
| Dow Corning Fluid 245/345 | + | + | + |
| Propylene Glycol | − | − | − |
| Finsolv BOD | + | + | + |
| Finsolv EMG-20 | − | − | − |
| Finsolv EB | + | + | + |
| Finsolv P | + | + | + |
| Finsolv PL-62 | + | + | + |
| Finsolv PL-355 | + | + | + |
| Finsolv PG-22 | + | + | + |
| Finsolv SB | + | + | + |
| Finsolv TN | + | + | + |
| Finester EH-25 | + | + | + |
| IPM/IPP (Witconol 2314/2316) | + | + | + |

KEY:
+ indicates soluble
− indicates insoluble

The two most commonly used solid organic crystalline sunscreens are Benzophenone-3 (2 hydroxy-4-methoxybenzophenone) and Parsol 1789 (butyl-methoxy dibenzoyl methane, also known as Avobenzone). These two solid sunscreens are difficult to dissolve and keep in solution for use in sunscreen formulations for optimal SPF (Sun Protection Factors). Higher solvency for a sunscreen ingredient is desired as it allows higher concentrations of the sunscreen active ingredient in a formulation. This advantageously raises the SPF ratings for the formulations. The liquid organic sunscreens that are commonly used are octylsalicylate (OS) and octyl-methoxycinnamate (OMC). Esters of this invention exhibit superiority over commonly used and marketed cosmetic emollients/materials.

The high solvency exhibited by the esters of the invention for the solid crystalline organic suncreens is an advantageous effect in formulating sunscreen products for the skin care markets. Thus, besides being cosmetic emollients, these esters are excellent solvents for the above-mentioned sunscreens.

A further aspect of these esters, besides being solubilizers for the sunscreens, is that they render antiwashoff effects. This effect is very attractive in formulating long-lasting sunscreen products allowing the sunscreen to remain on the skin for a longer duration.

Note: Dihydroxyacetone ("DHA") is a self-tanning agent, i.e., a chemical tanning agent.

Conclusion: The benzoate, octanoate, and maleate esters of monomethyl branched C16–C17 alcohols of the invention are more effective in dissolving solid organic sunscreens as compared to commercially available benzoate esters (i.e., Finester EH-25) and maleate esters (i.e., Finester LP).

EXAMPLE #4

Preparation of Sunscreen Creams (Ref. Nos. 134-34, 134-35, 134-36)

Esters of the invention, as prepared in Examples #1 through #3 above, will now be compared to commercially available esters. Table IV sets forth the ingredients used to prepare Formulations A through H, which are sunscreen creams.

TABLE III

SUNSCREEN SOLUBILITIES IN ESTERS (25° C.)

| Sunscreen | Benzoate Ref. No. 130-63 | Finsolv TN | Octanoate Ref. No. 130-67 | Finester EH-25 | Maleate Ref. No. 134-26 | Finester LP |
|---|---|---|---|---|---|---|
| Benzophenone-3 | 25 | 15 | 18 | 10 | 14 | 10 |
| Parsol 1789 | 18 | 13 | 10 | 7 | 9 | 6 |
| Dihydroxyacetone | 1 | <1 | 1 | <1 | <1 | <1 |
| Salicylic Acid | 5 | 3 | 1 | <1 | <1 | <1 |

Note:
The higher the value, the more soluble the ester.
Note:
Dihydroxyacetone ("DHA") is a self-tanning agent, i.e., a chemical tanning agent.
Conclusion:
The benzoate, octanoate, and maleate esters of monomethyl branched C16–C17 alcohols of the invention are more effective in dissolving solid organic sunscreens as compared to commercially available benzoate esters (i.e., Finsolv TN), octanoate esters (i.e., Finester EH-25) and maleate esters (i.e., Finester LP).

TABLE IV

FORMULATIONS A–H
SUNSCREEN CREAMS (REF. NOS. 134-34, 134-35, 134-36)

| | Ingredients/Trade Name | A | B | C | D | E | F | G | H |
|---|---|---|---|---|---|---|---|---|---|
| I | Water | 62 | 62 | 62 | 62 | 62 | 62 | 62 | 62 |
| | Polyglycol E400 | 5 | 5 | 5 | 5 | 5 | 5 | 5 | 5 |
| II | Benzoate Ester (130-63) | 7 | — | — | — | — | — | — | — |
| | Octanoate Ester (130-67) | — | 7 | — | — | — | — | — | — |
| | Maleate Ester (134-26) | — | — | 7 | — | — | — | — | — |
| | Finsolv TN | — | — | — | 7 | — | — | — | — |
| | Finester EH-25 | — | — | — | — | 7 | — | — | — |
| | Finester LP | — | — | — | — | — | 7 | — | — |
| | Witconol 2314 | — | — | — | — | — | — | 7 | — |
| | Finester DOM-R | — | — | — | — | — | — | — | 7 |
| | Finsolv EMG-20 | 6 | 6 | 6 | 6 | 6 | 6 | 6 | 6 |
| | Parsol MCX | 8 | 8 | 8 | 8 | 8 | 8 | 8 | 8 |
| | Escalol 567 | 3 | 3 | 3 | 3 | 3 | 3 | 3 | 3 |
| | Escalol 587 | 5 | 5 | 5 | 5 | 5 | 5 | 5 | 5 |
| | Crothix | 1 | 1 | 1 | 1 | 1 | 1 | 1 | 1 |
| | Cetal | 1 | 1 | 1 | 1 | 1 | 1 | 1 | 1 |
| | Cerasynt SD | 1 | 1 | 1 | 1 | 1 | 1 | 1 | 1 |
| III | Germaben II | 1 | 1 | 1 | 1 | 1 | 1 | 1 | 1 |

The procedure for preparing Formulations A–H of Table IV is as follows: Charge the ingredients of Part I, starting with water. Bring the temperature to 70° C. to 75° C. Mix well until uniform. Heat ingredients of Part II to 75° C. Add ingredients of Part II to Part I with mixing. Cool to 35° C. with gentle mixing. Add ingredients of Part III. Mix well and cool to 30° C.

Formulations A–H so prepared were tested for skin feel, emolliency, slip, and spreadability on a scale of 1 to 5, with 1 representing the best and 5 representing poor. Results are as follows:

TABLE IV-A

FORMULATIONS A–H
SUNSCREEN CREAM (REF. NOS. 134-34, 134-35, 134-36)

|  | A | B | C | D | E | F | G | H |
|---|---|---|---|---|---|---|---|---|
| Skin Feel | 1 | 1 | 2 | 3 | 4 | 4 | 5 | 5 |
| Emolliency | 1 | 1 | 1 | 3 | 3 | 4 | 5 | 5 |
| Slip | 1 | 1 | 2 | 3 | 4 | 4 | 5 | 5 |
| Spreadability | 1 | 2 | 2 | 3 | 3 | 4 | 5 | 5 |

Formulations A, B, and C (the benzoate, octanoate and maleate esters of the invention) gave superior skin feel, emolliency, slip and spreadability.

EXAMPLE #5

Preparation of Sunscreen Sticks (Ref. Nos. 134-41, 134-42, 134-43)

Table V sets forth the ingredients used to prepare Formulations A through H, which are sunscreen sticks.

TABLE V

FORMULATIONS A–H
SUNSCREEN STICKS (REF. NOS. 134-41, 134-42, 134-43)

| Ingredients/Trade Name | A | B | C | D | E | F | G | H |
|---|---|---|---|---|---|---|---|---|
| Witconol APM | 44 | 44 | 44 | 44 | 44 | 44 | 44 | 44 |
| Benzoate Ester (130-63) | 25 | — | — | — | — | — | — | — |
| Octanoate Ester (130-67) | — | 25 | — | — | — | — | — | — |
| Maleate Ester (134-26) | — | — | 25 | — | — | — | — | — |
| Finsolv TN | — | — | — | 25 | — | — | — | — |
| Finester EH-25 | — | — | — | — | 25 | — | — | — |
| Finester LP | — | — | — | — | — | 25 | — | — |
| Witconol 2314 | — | — | — | — | — | — | 25 | — |
| Finester DOM-R | — | — | — | — | — | — | — | 25 |
| Parsol MCX | 7.5 | 7.5 | 7.5 | 7.5 | 7.5 | 7.5 | 7.5 | 7.5 |
| Escalol 587 | 5.5 | 5.5 | 5.5 | 5.5 | 5.5 | 5.5 | 5.5 | 5.5 |
| Sodium Stearate C7 | 8 | 8 | 8 | 8 | 8 | 8 | 8 | 8 |
| Aminol HCA | 7 | 7 | 7 | 7 | 7 | 7 | 7 | 7 |
| Water | 3 | 3 | 3 | 3 | 3 | 3 | 3 | 3 |

The procedure for preparing Formulations A–H of Table V is as follows: Charge the ingredients in the order shown in Table V. Bring the temperature to 80° C. Mix well until uniform. Cool to 60° C. Pour into appropriate molds at 60° C.

Formulations A–H so prepared were tested for slip, spreadability, skin feel, emolliency, stickiness and water-rinseoff-resistance on a scale of 1 to 5, with 1 representing the best and 5 representing poor. Results are as follows:

TABLE V-A

FORMULATIONS A–H
SUNSCREEN STICKS (REF. NOS. 134-41, 134-42, 134-43)

|  | A | B | C | D | E | F | G | H |
|---|---|---|---|---|---|---|---|---|
| Slip | 1 | 1 | 2 | 3 | 4 | 4 | 5 | 5 |
| Spreadability | 1 | 2 | 3 | 3 | 3 | 4 | 5 | 4 |
| Skin Feel | 1 | 1 | 2 | 3 | 3 | 4 | 5 | 5 |
| Emolliency | 1 | 1 | 2 | 3 | 4 | 4 | 5 | 5 |
| Stickiness | 1 | 1 | 2 | 3 | 4 | 4 | 5 | 4 |
| Water-Rinseoff-Resistance | 1 | 2 | 2 | 3 | 4 | 4 | 5 | 5 |

Formulations A, B, and C (the benzoate, octanoate and maleate esters of the invention) exhibited superior slip, spreadability, skin feel, emolliency, stickiness and water-rinseoff resistence.

EXAMPLE #6

Preparation of Clear Sunscreen Oils (Ref. Nos. 134-47, 134-48, 134-49)

Table VI sets forth the ingredients used to prepare Formulations A through H, which are clear sunscreen oils.

TABLE VI

FORMULATIONS A–H
CLEAR SUNSCREEN OILS
(REF. NOS. 134-47, 134-48, 134-49)

| | Ingredients/Trade Name | A | B | C | D | E | F | G | H |
|---|---|---|---|---|---|---|---|---|---|
| I | Dow Corning Fluid 344 | 60 | 60 | 60 | 60 | 60 | 60 | 60 | 60 |
|  | Dow Corning Fluid 200 | 10 | 10 | 10 | 10 | 10 | 10 | 10 | 10 |
| II | Benzoate Ester (130-63) | 10 | — | — | — | — | — | — | — |
|  | Octanoate Ester (130-67) | — | 10 | — | — | — | — | — | — |
|  | Maleate Ester (134-26) | — | — | 10 | — | — | — | — | — |
|  | Finsolv TN | — | — | — | 10 | — | — | — | — |
|  | Finester EH-25 | — | — | — | — | 10 | — | — | — |
|  | Finester LP | — | — | — | — | — | 10 | — | — |
|  | Witconol 2314 | — | — | — | — | — | — | 10 | — |
|  | Finester DOM-R | — | — | — | — | — | — | — | 10 |
|  | Parsol MCX | 8 | 8 | 8 | 8 | 8 | 8 | 8 | 8 |
|  | Escalol 567 | 4 | 4 | 4 | 4 | 4 | 4 | 4 | 4 |
|  | Escalol 587 | 8 | 8 | 8 | 8 | 8 | 8 | 8 | 8 |

The procedure for preparing Formulations A–H of Table VI is as follows: Mix the ingredients of Part I and Part II separately, until uniform. When uniform, add the ingredients of Part II to the ingredients of Part I and stir at 25° C.

All formulations so prepared are clear liquids at 25° C. Formulations A–H so prepared were tested for slip, water-rinse-off-resistance, stickiness, skin feel, and emolliency on a scale of 1 to 5, with 1 representing the best and 5 representing poor. Results are as follows:

TABLE VI-A

FORMULATIONS A–H
CLEAR SUNSCREEN OILS
(REF. NOS. 134-47, 134-48, 134-49)

|  | A | B | C | D | E | F | G | H |
|---|---|---|---|---|---|---|---|---|
| Slip | 1 | 1 | 1 | 2 | 3 | 4 | 5 | 5 |
| Water-Rinse-Off Resistance | 1 | 2 | 2 | 3 | 3 | 4 | 5 | 4 |
| Stickiness | 1 | 1 | 2 | 3 | 3 | 4 | 5 | 4 |
| Skin Feel | 1 | 1 | 1 | 2 | 3 | 4 | 5 | 5 |
| Emolliency | 1 | 1 | 2 | 2 | 3 | 4 | 5 | 4 |

Formulations A, B, and C (the benzoate, octanoate and maleate esters of the invention) exhibited superior slip, water-rinseoff resistence, stickiness, skin feel and emolliency.

EXAMPLE #7

Preparation of Moisturizing Hand and Body Lotions (Ref. Nos. 134-29, 134-30, 134-31)

Table VII sets forth the ingredients used to prepare Formulations A through H, which are moisturizing hand and body lotions.

TABLE VII

FORMULATIONS A–H
MOISTUIRIZING HAND AND BODY LOTIONS
(Ref. Nos. 134-29, 134-30, 134-31)

| | Ingredients/Trade Name | A | B | C | D | E | F | G | H |
|---|---|---|---|---|---|---|---|---|---|
| I | Water | 85.95 | 85.95 | 85.95 | 85.95 | 85.95 | 85.95 | 85.95 | 85.95 |
| | Carbomer | 0.15 | 0.15 | 0.15 | 0.15 | 0.15 | 0.15 | 0.15 | 0.15 |
| | Methylparaben | 0.1 | 0.1 | 0.1 | 0.1 | 0.1 | 0.1 | 0.1 | 0.1 |
| | Propylparaben | 0.1 | 0.1 | 0.1 | 0.1 | 0.1 | 0.1 | 0.1 | 0.1 |
| | Sorbitol 70% | 2 | 2 | 2 | 2 | 2 | 2 | 2 | 2 |
| | Hampine NA4 | 0.2 | 0.2 | 0.2 | 0.2 | 0.2 | 0.2 | 0.2 | 0.2 |
| | Triethanolamine | 0.9 | 0.9 | 0.9 | 0.9 | 0.9 | 0.9 | 0.9 | 0.9 |
| II | Benzoate Ester (130-63) | 5 | — | — | — | — | — | — | — |
| | Octanoate Ester (130-67) | — | 5 | — | — | — | — | — | — |
| | Maleate Ester (134-26) | — | — | 5 | — | — | — | — | — |
| | Finsolv TN | — | — | — | 5 | — | — | — | — |
| | Finester EH-25 | — | — | — | — | 5 | — | — | — |
| | Finester LP | — | — | — | — | — | 5 | — | — |
| | Witconol 2314 | — | — | — | — | — | — | 5 | — |
| | Finester DOM-R | — | — | — | — | — | — | — | 5 |
| | Drakeol 9 | 1.6 | 1.6 | 1.6 | 1.6 | 1.6 | 1.6 | 1.6 | 1.6 |
| | Cetal | 0.7 | 0.7 | 0.7 | 0.7 | 0.7 | 0.7 | 0.7 | 0.7 |
| | Hysterene 9718 | 1.5 | 1.5 | 1.5 | 1.5 | 1.5 | 1.5 | 1.5 | 1.5 |
| | Cerysynt SD | 0.8 | 0.8 | 0.8 | 0.8 | 0.8 | 0.8 | 0.8 | 0.8 |
| | Promulgen G | 1 | 1 | 1 | 1 | 1 | 1 | 1 | 1 |

The procedure for preparing Formulations A–H of Table VII is as follows: Charge water and disperse Carbomer in it. Charge balance of Part I ingredients in order, until each is dissolved. After addition of Triethanolamine, heat to 65° C. Mix Part I ingredients together and heat to 60° C. Add Part II ingredients to Part I ingredients with good mixing to form an emulsion. Continue mixing while cooling to 25° C. All formulations are opaque flowable lotions with pH of 6.5.

Formulations A–H so prepared were tested for skin feel, slip, stickiness, long-lasting moisturizing effect and emolliency on a scale of 1 to 5, with 1 representing the best and 5 representing poor. Results are as follows:

TABLE VII-A

FORMULATIONS A–H
MOISTURIZING HAND AND BODY LOTIONS
(Ref. Nos. 134-29, 134-30, 134-31)

| | A | B | C | D | E | F | G | H |
|---|---|---|---|---|---|---|---|---|
| Skin Feel | 1 | 1 | 1 | 2 | 3 | 4 | 5 | 5 |
| Slip | 1 | 1 | 2 | 2 | 3 | 4 | 5 | 5 |
| Stickiness | 1 | 2 | 2 | 2 | 3 | 4 | 5 | 4 |
| Moisturizing Effect | 1 | 2 | 1 | 2 | 3 | 3 | 5 | 5 |
| Emolliency | 1 | 1 | 1 | 2 | 3 | 4 | 5 | 4 |

Formulations A, B, and C (the benzoate, octanoate and maleate esters of the invention) exhibited superior skin feel, slip, stickiness, moisturizing effect and emolliency.

EXAMPLE #8

Preparation of Elegant Skin Creme (Ref. Nos. 134-50, 134-51, 134-52)

Table VIII sets forth the ingredients used to prepare Formulations A through H, which are elegant skin cremes. The procedure for preparing Formulations A–H of Table VIII is as follows: Charge the ingredients of Part I, starting with water. Bring the temperature to 70° C. to 75° C. Mix well until uniform. Heat ingredients of Part II to 75° C. Add Part II ingredients to Part I ingredients with mixing. Cool to 25° C. with gentle mixing. All formulations are soft in appearance with pH of 6.6.

TABLE VIII

FORMULATIONS A–H
ELEGANT SKIN CRÈME
(Ref. Nos. 134-50, 134-51, 134-52)

| Ingredients/Trade Name | A | B | C | D | E | F | G | H |
|---|---|---|---|---|---|---|---|---|
| I Water | 75.4 | 75.4 | 75.4 | 75.4 | 75.4 | 75.4 | 75.4 | 75.4 |
| Finquat CT-P Cons | 1.2 | 1.2 | 1.2 | 1.2 | 1.2 | 1.2 | 1.2 | 1.2 |
| Triethanolamine | 0.2 | 0.2 | 0.2 | 0.2 | 0.2 | 0.2 | 0.2 | 0.2 |
| Glucamate SSE-20 | 1.8 | 1.8 | 1.8 | 1.8 | 1.8 | 1.8 | 1.8 | 1.8 |
| Solulan 16 | 5 | 5 | 5 | 5 | 5 | 5 | 5 | 5 |
| II Cerasynt SD | 1 | 1 | 1 | 1 | 1 | 1 | 1 | 1 |
| Glucate SS | 0.8 | 0.8 | 0.8 | 0.8 | 0.8 | 0.8 | 0.8 | 0.8 |
| Promulgen G | 2.6 | 2.6 | 2.6 | 2.6 | 2.6 | 2.6 | 2.6 | 2.6 |
| Sodium Stearate C7 | 3 | 3 | 3 | 3 | 3 | 3 | 3 | 3 |
| Benzoate Ester (130-63) | 9 | — | — | — | — | — | — | — |
| Octanoate Ester (130-67) | — | 9 | — | — | — | — | — | — |
| Maleate Ester (134-26) | — | — | 9 | — | — | — | — | — |
| Finsolv TN | — | — | — | 9 | — | — | — | — |
| Finester EH-25 | — | — | — | — | 9 | — | — | — |
| Finester LP | — | — | — | — | — | 9 | — | — |
| Witconol 2314 | — | — | — | — | — | — | 9 | — |
| Finester DOM-R | — | — | — | — | — | — | — | 9 |

Formulations A–H so prepared were tested for skin feel, slip, stickiness, and emolliency on a scale of 1 to 5, with 1 representing the best and 5 representing poor. Results are as follows:

TABLE VIII-A

FORMULATIONS A–H
ELEGANT SKIN CRÈME
(Ref. Nos. 134-50, 134-51, 134-52)

| | A | B | C | D | E | F | G | H |
|---|---|---|---|---|---|---|---|---|
| Skin Feel | 1 | 2 | 1 | 2 | 3 | 4 | 5 | 5 |
| Slip | 1 | 1 | 2 | 2 | 3 | 4 | 5 | 5 |
| Stickiness | 1 | 1 | 2 | 2 | 3 | 4 | 5 | 5 |
| Emolliency | 1 | 1 | 1 | 2 | 3 | 4 | 5 | 5 |

Formulations A, B, and C (the benzoate, octanoate and maleate esters of the invention) exhibited superior skin feel, slip, stickiness, and emolliency.

EXAMPLE #9

Preparation of Deodorant Sticks (Ref. Nos. 134-44, 134-45, 134-46)

Table IX sets forth the ingredients used to prepare Formulations A through H, which are deodorant sticks.

The procedure for preparing Formulations A–H of Table IX is as follows: Charge the ingredients in the order shown in Table IX, starting with propylene glycol. Bring the temperature to 80° C. allowing all to dissolve. Mix well until uniform. Cool to 60° C. and cast into stick molds.

TABLE IX

FORMULATIONS A–H
DEODORANT STICKS (Ref. Nos. 134-44, 134-45, 134-46)

| Ingredients/Trade Name | A | B | C | D | E | F | G | H |
|---|---|---|---|---|---|---|---|---|
| Propylene Glycol | 65 | 65 | 65 | 65 | 65 | 65 | 65 | 65 |
| Water | 15 | 15 | 15 | 15 | 15 | 15 | 15 | 15 |
| Sodium Stearate C7 | 8 | 8 | 8 | 8 | 8 | 8 | 8 | 8 |
| Brij 78 | 8 | 8 | 8 | 8 | 8 | 8 | 8 | 8 |
| Benzoate Ester (130-63) | 3.8 | — | — | — | — | — | — | — |
| Octanoate Ester (130-67) | — | 3.8 | — | — | — | — | — | — |
| Maleate Ester (134-26) | — | — | 3.8 | — | — | — | — | — |
| Finsolv TN | — | — | — | 3.8 | — | — | — | — |
| Finester EH-25 | — | — | — | — | 3.8 | — | — | — |
| Finester LP | — | — | — | — | — | 3.8 | — | — |
| Witconol 2314 | — | — | — | — | — | — | 3.8 | — |
| Finester DOM-R | — | — | — | — | — | — | — | 3.8 |
| Torclosan | 0.2 | 0.2 | 0.2 | 0.2 | 0.2 | 0.2 | 0.2 | 0.2 |

Formulations A–H so prepared were tested for emolliency, slip, and soft dry afterfeel on a scale of 1 to 5, with 1 representing the best and 5 representing poor. Results are as follows:

TABLE IX-A

FORMULATIONS A–H
DEODORANT STICKS (Ref. Nos. 134-44, 134-45, 134-46)

| | A | B | C | D | E | F | G | H |
|---|---|---|---|---|---|---|---|---|
| Emolliency | 1 | 1 | 1 | 2 | 3 | 3 | 5 | 4 |
| Slip | 1 | 1 | 2 | 2 | 2 | 3 | 5 | 4 |
| Soft Dry After-feel | 1 | 1 | 1 | 2 | 2 | 3 | 5 | 4 |

Formulations A, B, and C (the benzoate, octanoate and maleate esters of the invention) exhibited superior emolliency, slip and soft dry after-feel.

EXAMPLE #10

Preparation of Non-Whitening Antiperspirant Sticks
(Ref. Nos. 134-38, 134-39, 134-40)

Table X sets forth the ingredients used to prepare Formulations A through H, which are non-whitening antiperspirant sticks.

The procedure for preparing Formulations A–H of Table X is as follows: Charge the ingredients of Part I, staring with Dow Corning Fluid 345. Bring the temperature to 75° C. Mix well until uniform. Add Part II powders and mix until completely dispersed. Maintain temperature of 75° C. Cool to 55° C. and cast into stick molds.

TABLE X

FORMULATIONS A–H
NON-WHITENING ANTIPERSPIRANT STICKS
(Ref. Nos. 134-38, 134-39, 134-40)

| | Ingredients/Trade Name | A | B | C | D | E | F | G | H |
|---|---|---|---|---|---|---|---|---|---|
| I | Dow Corning 345 Fluid | 39 | 39 | 39 | 39 | 39 | 39 | 39 | 39 |
| | Adol 62 | 18 | 18 | 18 | 18 | 18 | 18 | 18 | 18 |
| | Castorwax MP-70 | 5 | 5 | 5 | 5 | 5 | 5 | 5 | 5 |
| | Benzoate Ester (130-63) | 5 | — | — | — | — | — | — | — |
| | Octanoate Ester (130-67) | — | 5 | — | — | — | — | — | — |
| | Maleate Ester (134-26) | — | — | 5 | — | — | — | — | — |
| | Finsolv TN | — | — | — | 5 | — | — | — | — |
| | Finester EH-25 | — | — | — | — | 5 | — | — | — |
| | Finester LP | — | — | — | — | — | 5 | — | — |
| | Witconol 2314 | — | — | — | — | — | — | 5 | — |
| | Finester DOM-R | — | — | — | — | — | — | — | 5 |
| | Finsolv 116 | 10 | 10 | 10 | 10 | 10 | 10 | 10 | 10 |
| II | Reach AZP - 908 | 20 | 20 | 20 | 20 | 20 | 20 | 20 | 20 |
| | Talc | 2 | 2 | 2 | 2 | 2 | 2 | 2 | 2 |
| | Silica | 1 | 1 | 1 | 1 | 1 | 1 | 1 | 1 |

Formulations A–H so prepared were tested for emolliency, stickiness, talc-like feel, and stick structure on a scale of 1 to 5, with 1 representing the best and 5 representing poor. Results are as follows:

TABLE X-A

FORMULATIONS A–H
NON-WHITENING ANTIPERSPIRANT STICKS
(Ref. Nos. 134-38, 134-39, 134-40)

| | A | B | C | D | E | F | G | H |
|---|---|---|---|---|---|---|---|---|
| Emolliency | 1 | 1 | 2 | 2 | 3 | 3 | 5 | 4 |
| Stickiness | 1 | 1 | 1 | 2 | 2 | 3 | 5 | 5 |
| Talc-like Feel | 1 | 1 | 1 | 2 | 2 | 3 | 5 | 4 |
| Stick Structure | 1 | 1 | 1 | 2 | 3 | 3 | 5 | 5 |

Formulations A, B, and C (the benzoate, octanoate and maleate esters of the invention) exhibited superior emolliency, stickiness, talc-like feel and stick structure.

Table XI is a Table of Identification which identifies products both known and produced by the process of this invention. For ease of identification, each ester is identified by a Trade Name, where available. This identification system is used in the above Tables and Examples.

TABLE XI

Identification of Trade Names/Sources

| Trade/Generic Material | Identification | Source |
|---|---|---|
| Ref. No. 130-63 | C16–C17 Alkyl Benzoate | Finetex Inc., NJ |
| Ref. No. 130-67 | C16–C17 Alkyl Octanoate | Finetex Inc., NJ |
| Ref. No. 134-26 | Di C12–C15 Alkyl Maleate | Finetex Inc., NJ |
| Finester EH-25 | C12–C15 Alkyl Octanoate | Finetex Inc., NJ |
| Finester LP | Di C12–C15 Alkyl Maleate | Finetex Inc., NJ |
| Finester DOM-R | Dioctyl Maleate | Finetex Inc., NJ |
| Finquat CT-P Cons | Quaternium 89 | Finetex Inc., NJ |
| Finsolv BOD | Octyldodecyl Benzoate | Finetex Inc., NJ |
| Finsolv EB | Ethylhexyl Benzoate | Finetex Inc., NJ |
| Finsolv EMG-20 | Methyl Gluceth –20 Benzoate | Finetex Inc., NJ |
| Finsolv P | PPG-15 Stearyl Ether Benzoate | Finetex Inc., NJ |
| Finsolv PG22 | Dipropylene Glycol Dibenzoate | Finetex Inc., NJ |
| Finsolv PL 62 | Poloxamer 182 Dibenzoate | Finetex Inc., NJ |
| Finsolv PL 355 | Poloxamer 105 Benzoate | Finetex Inc., NJ |
| Finsolv SB | Isostearyl Benzoate | Finetex Inc., NJ |
| Finsolv TN | C12–C15 Alkyl Benzoate | Finetex Inc., NJ |
| Finsolv 116 | Stearyl Benzoate | Finetex Inc., NJ |
| Aminol HCA | Cocoamide DEA | Finetex Inc., NJ |
| Adol 62 | Stearyl Alcohol | Witco Corp., Texas |
| Brij 78 | Steareth-20 | ICI, DE |
| Carbomer | Carpopol ETD 2001 Resin | B. F. Goodrich, OH |
| Castorwax MP-70 | Hydrogenated Castor Oil | Cas Chem, NJ |
| Cerasynt SD | Glyceryl Stearate | ISP, N.J. |
| Cetal | Cetyl Alcohol | Amerchol Edison, NJ |
| Crothix | PEG 150 Pentaerythirtyl Tetrastearate | Croda, Inc., NJ |
| Dow Corning Fluid 200 | Dimethicone | Dow Corning, MI |
| Dow Corning Fluid 344 | Cyclomethicone | Dow Corning, MI |
| Dow Corning Fluid 345 | Cyclomethicone | Dow Corning, MI |
| Drakeol 9 | Light Mineral Oil | Panorco, PA |

TABLE XI-continued

Identification of Trade Names/Sources

| Trade/Generic Material | Identification | Source |
|---|---|---|
| Escalol 567 | Benzopherone 3 | ISP, NJ |
| Escalol 587 | Octylsalicylate | ISP, NJ |
| Germaben II | Diazolidinyl urea | ISP, NJ |
| Glucamate SSE-20 | PEG-20 Methyl Glucose Sesquistearate | Amerchol Edison, NJ |
| Glucate SS | Methyl Glucose Sesquistearate | Amerchol Edison, NJ |
| Hampine Na4 | Ethylene Diamine Tetraacetic, Sod. Salt | Hampshire Chem. Corp., NH |
| Hystrene 9718 | Stearic Acid | Witco Corp, TX |
| Parsol MCX | Octylmethoxycinnamate | Roche Vitamins, NJ |
| Polyglycol E400 | Polyethylene Glycol 400 | D. V. C. Limited, Inc., NJ |
| Promulgen G | Stearyl Alcohol & Ceteareth-20 | Amerchol Edison, NJ |
| Reach AZP 908 | Aluminum Zirconium Tetrachloro-Gly | Reheis, Inc., NJ |
| Silica | Cabosil M - 5 | Cabot Corp., NJ |
| Sodium Stearate C7 | Sodium Stearate | Witco Corp, TX |
| Solulan 16 | Lanath-16, Celeth 16, Oleth 16 & Steareth | Americhol Edison, NJ |
| Triclosan | Irgason DP 300 | Ciba Geigy, NC |
| Witconol 2314 | Iso Propyl Myristate | Witco Corp, TX |
| Witconol APM | PPG-3 Myristyl Ether | Witco Corp, TX |

In conclusion, the esters of the invention, namely, the benzoate, octanoate, and maleate esters of monomethyl branched C16–C17 alcohols, are superior in skin feel, emolliency, slip, stickiness, moisturizing effect, etc. as compared to known esters.

It is understood that the embodiments described herein are merely exemplary and that a person skilled in the art may make many variations and modifications without departing from the spirit and scope of the invention. All such modifications and variations are intended to be included within the scope of the invention described herein.

We claim:

1. A benzoate ester of branched monomethyl C16 and C17 alcohol having the structure:

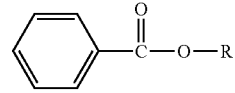

where R=monomethyl branched C16–C17 alkyl.

2. An octanoate ester of branched monomethyl C16 and C17 alcohol having the structure:

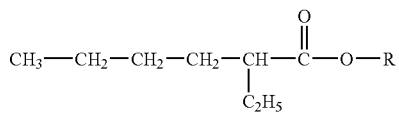

where R=monomethyl branched C16–C17 alkyl.

3. The benzoate ester of claim 1 which is prepared by the esterification of benzoic acid and branched monomethyl C16 and C17 alcohol having the structure:

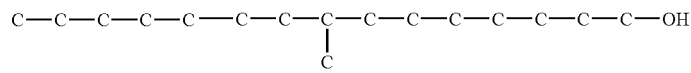

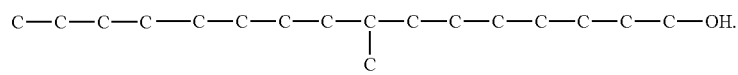

4. The octanoate ester of claim 2 which is prepared by the esterification of 2-ethyl hexanoic acid and branched monomethyl C16 and C17 alcohol having the structure:

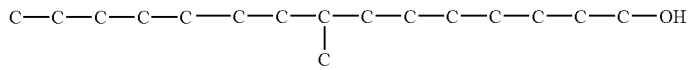

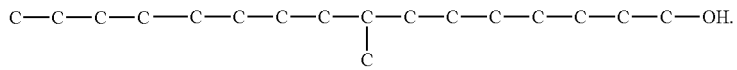

5. A method of preparing the benzoate ester of claim 1 comprising reacting benzoic acid with branched monomethyl C16 and C17 alcohol having the structure:

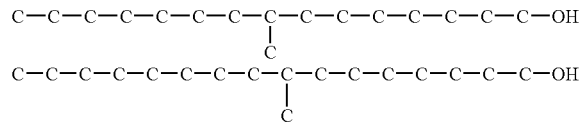

6. A method of preparing the octanoate ester of claim 2 comprising reacting 2-ethyl hexanoic acid with branched monomethyl C16 and C17 alcohol having the structure:

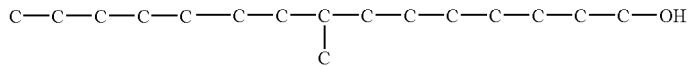

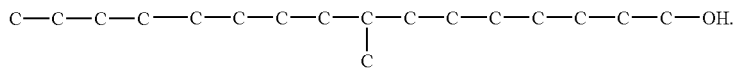

7. A sunscreen composition comprising an effective amount of the benzoate ester of claim 1.

8. A sunscreen composition comprising an effective amount of the octanoate ester of claim 2.

9. An antiperspirant composition comprising an effective amount of the benzoate ester of claim 1.

10. An antiperspirant composition comprising an effective amount of the octanoate ester of claim 2.

11. A skin or hair care preparation comprising an effective amount of the benzoate ester of claim 1.

12. A skin or hair care preparation comprising an effective amount of the octanoate ester of claim 2.

13. A method of blocking the effects of the sun on human skin or hair comprising applying to the skin or hair a formulation comprising an effective amount of a sunscreen composition according to claim 7.

14. A method of blocking the effects of the sun on human skin or hair comprising applying to the skin or hair a formulation comprising an effective amount of a sunscreen composition according to claim 8.

15. A skin or hair care method comprising applying to the skin or hair a formulation comprising a benzoate ester according to claim 1.

16. A skin or hair care method comprising applying to the skin or hair a formulation comprising an octanoate ester according to claim 2.

17. The composition of claim 7 further comprising one or more components selected from the group consisting of surfactants, neutralizers, stabilizers, coloring agents, fragrances, plasticizers, foam stabilizers, film forming polymers, preservatives, antistats, sequestrants, water, dyes, perfume, thickeners, preservatives, plant extracts, and customary additive and auxiliary substances.

18. The composition of claim 8 further comprising one or more components selected from the group consisting of surfactants, neutralizers, stabilizers, coloring agents, fragrances, plasticizers, foam stabilizers, film forming polymers, preservatives, antistats, sequestrants, water, dyes, perfume, thickeners, preservatives, plant extracts, and customary additive and auxiliary substances.

* * * * *